United States Patent [19]

Makino et al.

[11] Patent Number: 5,129,400
[45] Date of Patent: Jul. 14, 1992

[54] OPHTHALMOLOGICAL MEASUREMENT METHOD AND APPARATUS

[75] Inventors: Misao Makino, Hachiouji; Kiyoshi Hashimoto; Toshiaki Sugita, both of Hino, all of Japan

[73] Assignee: Kowa Company Ltd., Japan

[21] Appl. No.: 507,399

[22] Filed: Apr. 9, 1990

[30] Foreign Application Priority Data

Apr. 10, 1989 [JP] Japan ................. 1-87856
Apr. 12, 1989 [JP] Japan ................. 1-90787

[51] Int. Cl.$^5$ .................................. A61B 3/113
[52] U.S. Cl. ................................. 128/666; 128/691; 351/206; 351/210; 351/221; 356/28.5
[58] Field of Search ............... 128/691, 661.1, 666; 356/28.5; 351/206, 209, 210, 211, 221

[56] References Cited

U.S. PATENT DOCUMENTS

| | | | |
|---|---|---|---|
| 4,346,991 | 8/1982 | Gardner et al. | 128/691 |
| 4,402,601 | 9/1983 | Riva | 128/666 |
| 4,443,075 | 4/1984 | Crane | 351/209 |
| 4,848,897 | 7/1989 | Aizu et al. | 128/691 |
| 4,856,891 | 8/1989 | Pflibsen et al. | 351/206 |
| 4,972,836 | 11/1990 | Schenck et al. | 128/653 |

*Primary Examiner*—Ruth S. Smith
*Attorney, Agent, or Firm*—Bruce L. Adams; Van C. Wilks

[57] ABSTRACT

In an ophthalmological measurement method and apparatus, a laser beam of predetermined diameter is projected to the eye fundus and movement of a speckle pattern formed by light scattered by blood cells in blood vessel is detected by a photosensor as fluctuation in speckle light intensity to produce a speckle signal. The speckle light intensity will fluctuate more rapidly with a smaller output from the photosensor when cell velocities are high, while a low cell travel speed will decrease the lowering of the output therefrom. The speckle signal thus mirrors the travel speed of the blood cells in the eye tissues. The differences in the speckle signal are used to identify the blood vessel for automatic tracking of the blood vessel or for measurement of its diameter.

17 Claims, 8 Drawing Sheets

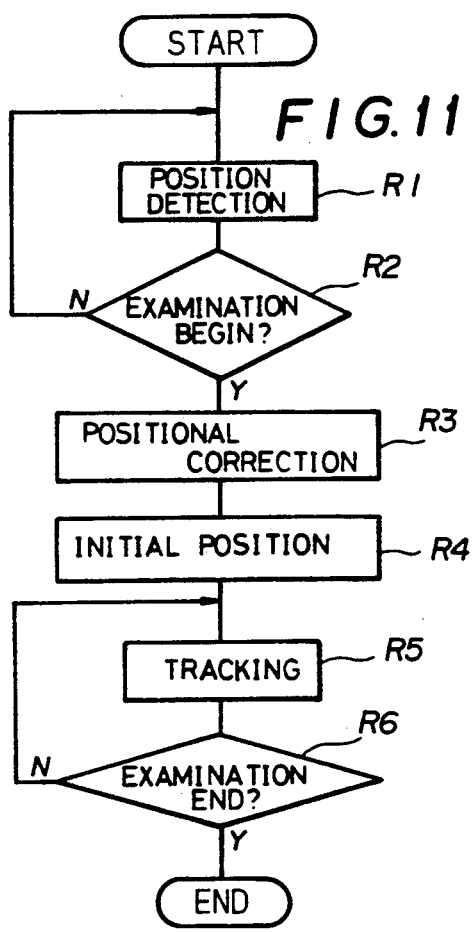
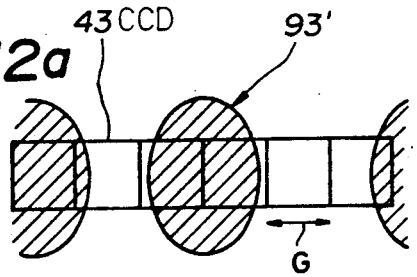
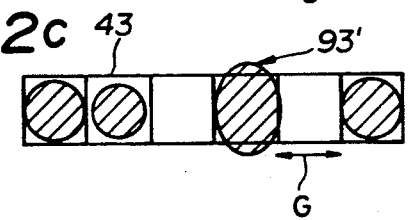
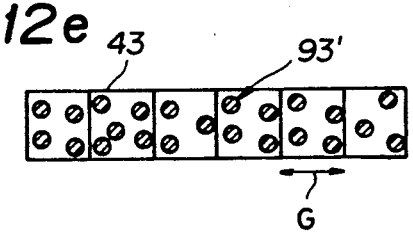
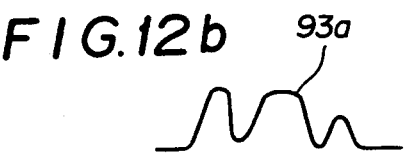
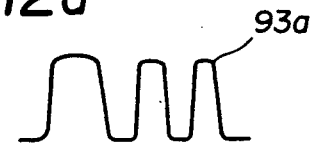
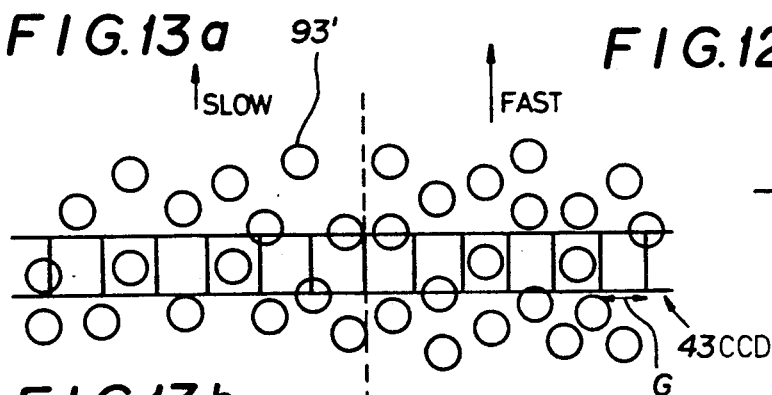
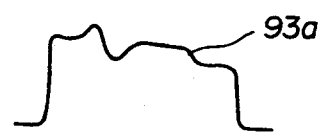
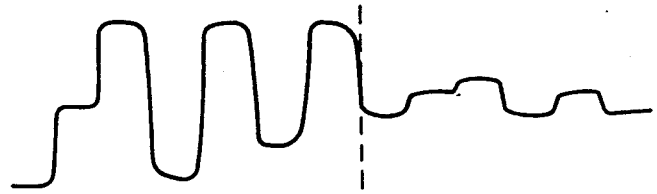

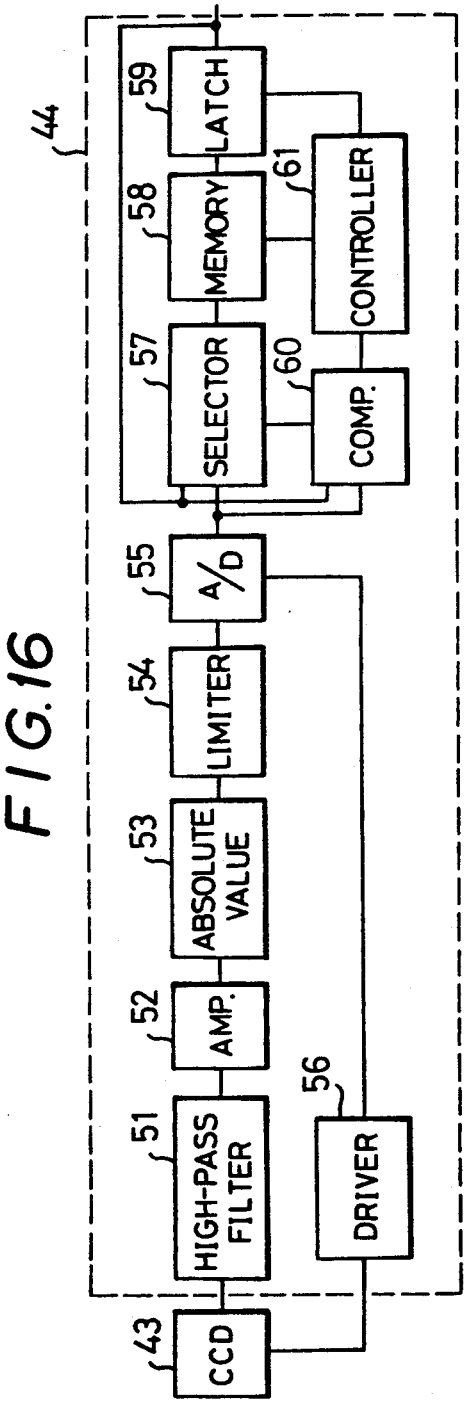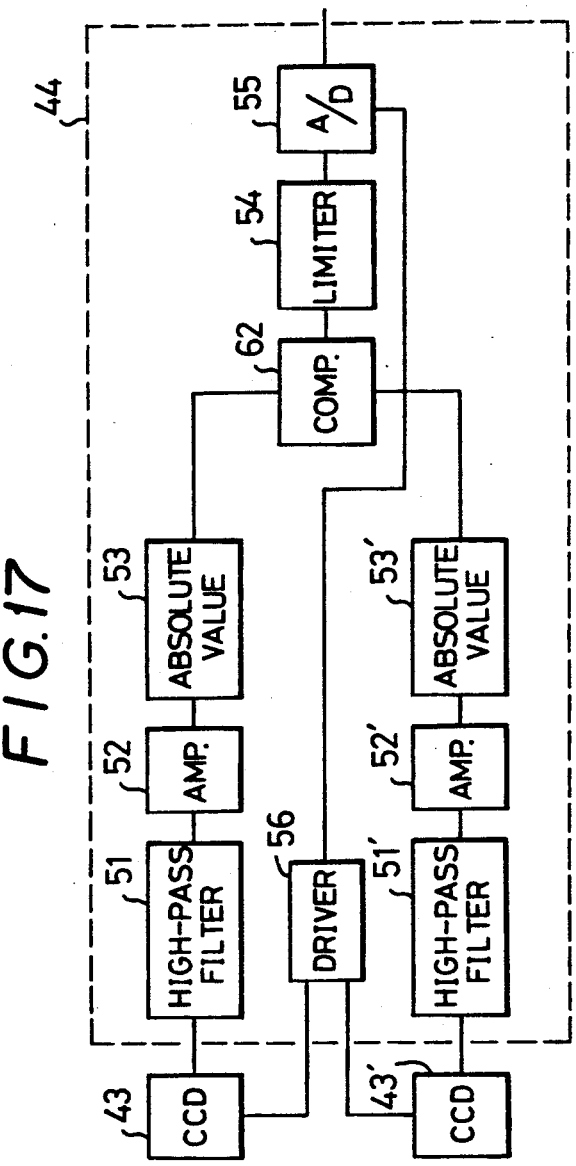

OPHTHALMOLOGICAL MEASUREMENT METHOD AND APPARATUS

BACKGROUND OF THE INVENTION

1. Field of the Invention

This invention relates to an ophthalmological measurement method and apparatus, and more particularly to an ophthalmological measurement method and apparatus in which the eye fundus is illuminated by a laser beam having a predetermined diameter and motion of a laser speckle pattern formed by laser light scattered and reflected from the eye fundus is detected at an observation point as fluctuations in the speckle light intensity to produce a speckle signal which is evaluated for ophthalmological measurement.

2. Description of the Prior Art

Various conventional methods are used for ophthalmological measurement. These conventional methods include illuminating the eye fundus with a laser beam, detecting the light scattered by the eye fundus and analyzing and evaluating this light. There are, for example, laser Doppler methods for measuring blood flow in retinal and other tissue described in "Investigative Ophthalmology," vol. 11 No. 11, page 936 (November 1972) and "Science," vol.186 (November 1974) page 830, and in Japanese Unexamined Patent Publication Nos. 55-75668, 55-75669, 55-75670, 52-142885 (corresponding to GB 13132/76 and U.S. Pat. No. 4,166,695), 56-125033 (corresponding to GB 79/37799), 58-118730 (corresponding to U.S. Pat. No. 4,402,601) and U.S. Pat. No. 4,142,796. However, these laser Doppler methods involve the use of a high precision optical system, are complicated to use and provide results which lack repeatability and reliability, all of which make practical application difficult.

It is known that when a laser beam strikes an object which causes diffusion or scattering of the beam, the light scattering from the object gives rise to a speckle pattern caused by interference between reflected rays of the coherent light. The laser speckle method utilizes this to evaluate the state of tissues in the eye fundus. Examples of this method are described in Japanese Unexamined Patent Publication Nos. 62-275431 (U.S. Pat. No. 4,734,107 and EPC 234869), 63-238843 (EPC 284248) and 63-242220 (EPC 285314).

These publications describe the use of a detecting aperture to extract time-base fluctuations in the intensity of speckles formed at an optical Fourier Transform plane with respect to the eye fundus, or at the Fraunhofer refraction plane, or at an image plane (or a magnified image plane) that is conjugate with respect to the eye fundus, and the blood flow state is determined by an evaluation of the speckle signal thus obtained.

A major obstacle to the clinical application of the above systems has been their susceptibility to the effects of movement, such as movement of the subject's eye, vibration and the like. This frequently causes unwanted movement of speckle patterns on the detection plane, thus throwing the detecting aperture and laser beam out of alignment during measurement. One way to overcome this is described in the laser-Doppler method of Japanese Patent Publication No. 56-125033. This involves the mechanical scanning the eye fundus image on the detection plane and using differences between the light reflectance of the walls of a blood vessel and that of other areas of tissue to distinguish blood vessels, and correcting for positional deviation. A drawback of this method is that it requires a mechanism for the mechanical scanning of the eye fundus image, which makes the apparatus too large and complex to be practical.

Another method, described in Applied Optics, Vol. 27, No. 6, page 1113 (Mar. 15, 1988) and in Japanese Patent Publication No. 63-288133 (U.S. Pat. No. 014,994), shows the feasibility of an image scanning arrangement which allows blood vessels to be distinguished and tracked automatically. However, the method is based on the wavelength dependency of reflected light and relies for its implementation on a plurality of laser beams of different wavelengths which are projected in sequence. Again, this makes the apparatus complex, impractical and costly. A further drawback is that when corneal reflection is used to detect eye movement, the detection precision is not high enough for the purposes of correcting for movement by the blood vessel.

Conventional tracking methods involving the detection of eye movement include one in which the corneal surface is illuminated by a laser beam and movement of the reflected light is used to detect and track such eye movement another method uses differences between two images of the eye fundus obtained by a TV camera or other such imaging means.

However, such methods involve detection of eye surface movement and are only able to provide a low level of intraocular tracking precision. Moreover, eye fundus images obtained via a TV camera usually suffer from a poor S/N ratio because the amount of available light is insufficient, further the apparatus required to detect movement based on differences between two images is large and complex.

On the other hand, the speckle pattern moves as the scattering object moves, so that it is proposed to detect its movement as a fluctuation in the light intensity at the observation point to obtain the difference of the traveling speed of the object depending on the signal intensity.

To discriminate the blood vessel and measure the diameter of the blood vessel, there has been proposed a method in which the eye fundus is photographed using a fundus camera to measure the diameter of the blood vessel on the basis of the photographed eye fundus or a method in which a television camera is used to take a picture of the eye fundus and the eye fundus image is subjected to an image processing (for example, image sampling, A/D converting, sharping, masking, filtering) to determine the diameter of the blood vessel.

Such conventional methods require a long time to obtain measurement results because the eye fundus must be photographed, thus making it impossible to make real time measurement of the diameter of the blood vessel. Furthermore, the eye fundus image taken by the television camera is usually underexposed and has a poor S/N ratio. This necessitates complicated image processing and results in a bulky and expensive apparatus.

SUMMARY OF THE INVENTION

It is therefore an object of the invention to provided an improved ophthalmological measurement method and apparatus employing the laser speckle phenomenon which is simple and straightforward in construction and is able to detect eye movement and automatically track the movement in the eye fundus with good accuracy.

It is another object of the invention to provided an improved ophthalmological measurement method and apparatus employing the laser speckle phenomenon which is simple and straightforward in construction and is able to accurately measure the diameter of the blood vessel.

The invention provides an ophthalmological measurement method and apparatus in which the eye fundus is illuminated by a laser beam projected by projecting means and having a predetermined diameter. Motion of a laser speckle pattern formed by laser light scattered and reflected from the eye fundus is detected at an observation point as fluctuations in the speckle light intensity to produce a speckle signal which is evaluated by evaluating means for ophthalmological measurement. In this arrangement the speckle signal is evaluated to discriminate differences in travel velocities of blood cells in the eye fundus to identify a blood vessel of the eye fundus.

Any movement of the identified blood vessel of the eye fundus is detected, and the position of the region illuminated by the laser beam and the position of the observation point are adjusted by positioning means by an amount corresponding to the amount of blood vessel movement to track the blood vessel automatically. Furthermore, both edges of the identified blood vessel are located to determine the diameter thereof.

In such an arrangement, the laser beam of predetermined diameter is projected into the eye fundus by a laser beam projector and the movement of a speckle pattern formed by diffused light scattered by blood cells within the eye tissue passes through a light receiving system and is detected by a photosensor as fluctuation in speckle light intensity. The speckle signal mirrors the travel speed of the blood cells in the eye tissues. The size of speckles on the photosensor and the scanning speed of the photosensor are optimally set. The speckle light intensity will fluctuate more rapidly when cell velocities are high, and the averaging effect of the photosensor's storage time will result in a smaller output. Conversely, a low cell travel speed will decrease the lowering of the output from the photosensor. The differences in signal intensity thus produced are used to distinguish blood vessels. Movable mirrors are driven by an amount corresponding to shifts in the position of the blood vessel caused, for example, by eye movement, so that the position of the region illuminated by the laser beam and the observation position are controlled to automatically track the blood vessel. Furthermore, both edges of the identified blood vessel are located to determine the diameter of the blood vessel. Thus, the invention provides an improved ophthalmological measurement method and apparatus which is able to detect eye movement and automatically track the movement in the eye fundus or measure the diameter of the blood vessel with a simplified structure and with good accuracy.

BRIEF DESCRIPTION OF THE DRAWINGS

The objects and features of the present invention will become more apparent from a consideration of the following detailed description taken in conjunction with the accompanying drawings in which:

FIG. 11 is a flow chart of the control process for central position correction;

FIGS. 12a to 12f are diagrams showing the relationship between speckle size and CCD pixel size, and output signals;

FIGS. 13a and 13b are graphs showing speckle pattern travel speed and the waveform of a CCD output signal;

FIGS. 16 and 17 are schematic views of a signal processor;

DETAILED DESCRIPTION OF THE PREFERRED EMBODIMENTS

Figure 1:
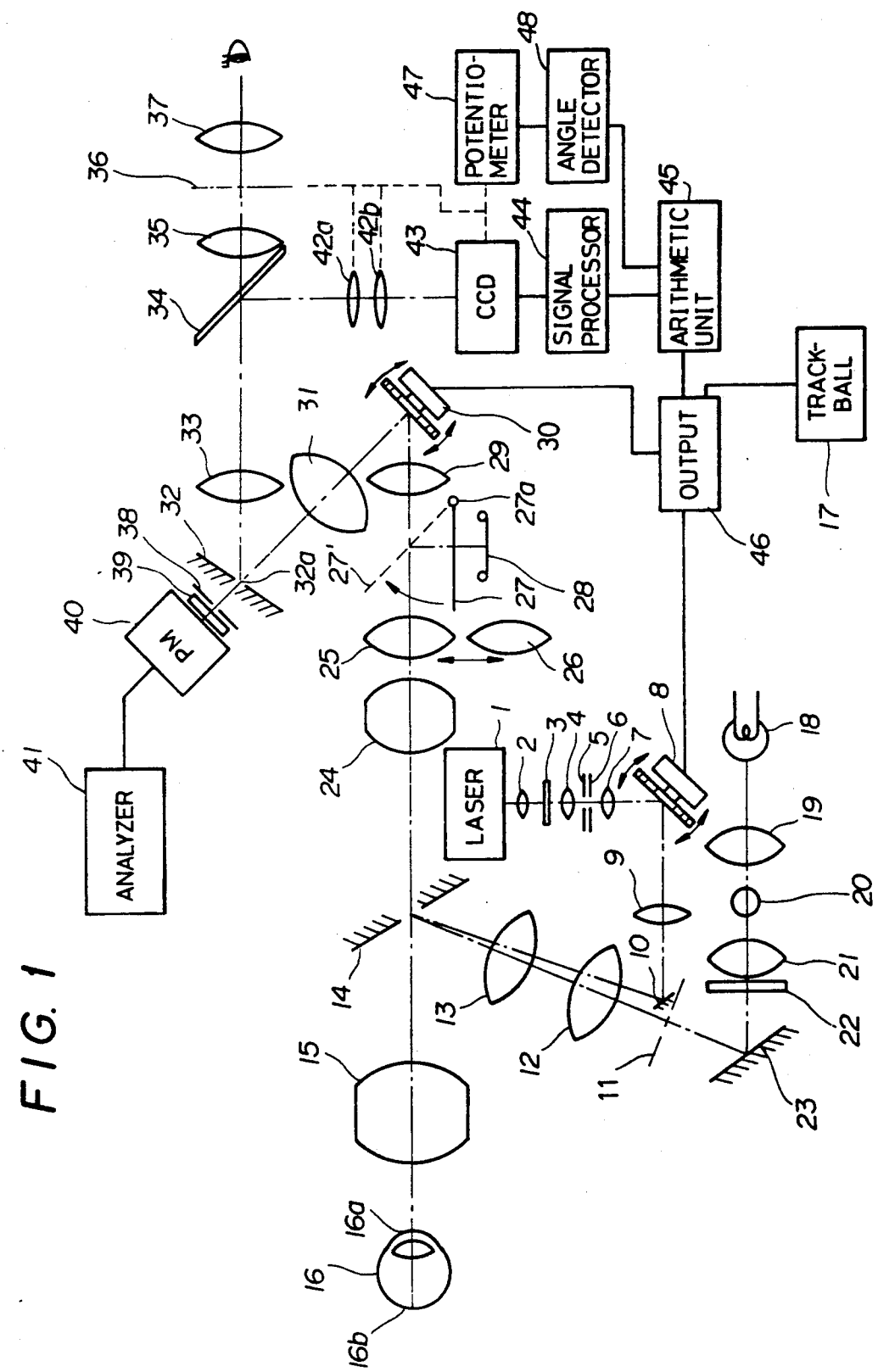
FIG. 1 is a diagram showing the structure of a first embodiment of an apparatus according to the present invention.

The invention will now be described in detail with reference to embodiments shown in the drawings.

The invention is particularly used for an ophthalmological measurement apparatus in which the eye fundus is illuminated by a laser beam having a prescribed diameter and motion of a laser speckle pattern formed by laser light scattered and reflected from the eye fundus is detected at an observation point as fluctuations in the speckle light intensity to produce a speckle signal which is evaluated to measure a blood flow state in tissues in the eye fundus. Therefore, the embodiments described below are those which are applied to the ophthalmological measurement apparatus including a basic optical arrangement of an eye fundus camera to measure the blood flow state in the eye fundus tissue. The invention is, however, not limited to such embodiments and may be applied to other type of ophthalmological apparatus.

With reference to FIG. 1, a laser beam from a red-light He-Ne (wavelength: 632.8 nm) laser light source 1, for example, passes through a condenser lens 2 and a light quantity adjustment filter 3 for adjusting the beam intensity, and is then collimated by a collimator lens 4. Two apertures 5 and 6 are provided within the path of the beam for selectively adjusting the size and shape of the region of an eye fundus 16b of a subject's eye 16 which is illuminated by the laser beam. The laser beam passes from the two aperatures 5 and 6 through lens 7 and is reflected by swingable mirror 8.

Figure 2:
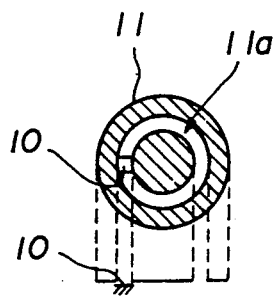
FIG. 2 is a diagram for explaining the structure of a ring slit.

The laser beam passes through a condenser lens 9 and is reflected by a mirror 10 provided in a transparent portion of an annular aperture 11a formed in a ring slit 11 arranged in an eye fundus camera illuminating projector, as shown in FIG. 2 (in which the non-transparent portion is indicated by shading). Such an arrangement enables the laser beam to direct along the same optical path to the eye fundus as that followed by the beam of light projected into the eye fundus to provide illumination for photography and observation. The laser beam thus passes through relay lenses 12 and 13, is reflected by a ring mirror 14 and, via an objective lens 15, passes through the cornea 16a of the eye under examination 16 to the eye fundus 16b where the blood vessel of interest is irradiated with the laser beam for measurement and tracking.

The swingable mirror 8 is provided in the optical laser beam illumination system to deflect the laser beam spot in the eye fundus 16b. Prior to the start of measurement, this deflection is performed via an output section 46 using means such as a trackball 17. The swingable mirror 8 can be controlled by an ordinary method such as a coagulator arrangement which allows independent control of the angle of mirror deflection in the x and y directions relative to the optical axis.

To minimize the discrepancy that has to be corrected arising from differences in laser beam deflection angles in the x and y directions, the angle at which the laser beam is reflected by the swingable mirror 8 is made as small as space will permit. The swingable mirror 8 is disposed at a position that is substantially a conjugate of the cornea 16a or pupil of the eye. This assures that the laser beam can be moved over the eye fundus without any major change in the position of beam incidence on the cornea.

The laser beam is provided on the same optical path as the photography and observation light beam. This arrangement is highly convenient since it enables the location within the eye fundus 16b at which the laser beam is being projected by the swingable mirror 8 to be brought within the field of view for photography or observation by using mechanisms for swinging and tilting the eye fundus camera vertically and horizontally and the eye fixation means.

This measurement and tracking region is also illuminated by an illuminating projector of the fundus camera to facilitate observation. The system for providing the illumination for observation includes an observation light source 18, a condenser lens 19, a condenser lens 21, a filter 22 and a mirror 23 disposed on the same light path as a photographic light source 20.

Figure 3:
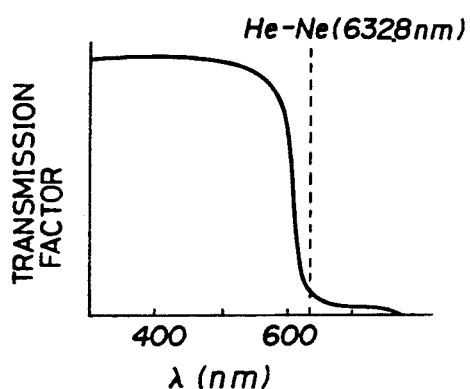
FIG. 3 is a characteristic curve showing the characteristics of a filter.

The filter 22 disposed between the condenser lens 21 and the mirror 23 is a wavelength separation filter having the type of characteristics shown in FIG. 3 to filter out red components from the observation and photographic light. A filter is selected that has spectral characteristics appropriate to the wavelength of the laser beam source that is employed.

Speckle light produced by the scattering of the laser beam in the eye fundus and reflected observation and photographic light passes through the objective lens 15, the ring mirror 14, a focusing lens 24, an imaging lens 25 or 26 and a relay lens 29, is reflected by a movable mirror 30 and passes through a relay lens 31 and is thereby formed into an image at a ring mirror 32. The light reflected by the ring mirror 32 passes through a relay lens 33 and is divided by a wavelength separation mirror 34. Cylindrical imaging lenses 42a and 42b form speckle light reflected by the wavelength separation mirror 34 into an image on a scanning type sensor CCD 43. The wavelength separation mirror 34 is set at an angle of about 45 degrees relative to the optical axis and as the wavelength separation mirror 34 has the same kind of spectral characteristics as wavelength separation filter 22, shown in FIG. 3, it reflects most of the speckle light produced by the red He-Ne laser beam.

Light that is transmitted by the wavelength separation mirror 34 passes through an imaging lens 35 and forms an image at a reticle 36. The examiner can view this image through an eyepiece 37. The eyepiece 37 can be adjusted to compensate for individual differences in visual acuity. The reticle 36 is used as a reference for such adjustments.

Figure 4:
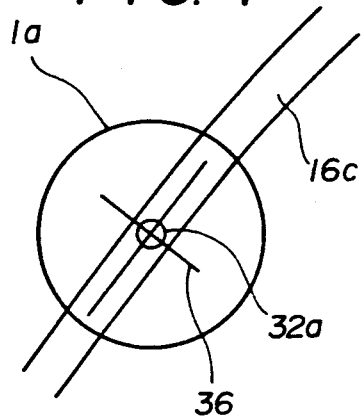
FIGS. 4 and 5 show observed images of the eye fundus.
Figure 5:
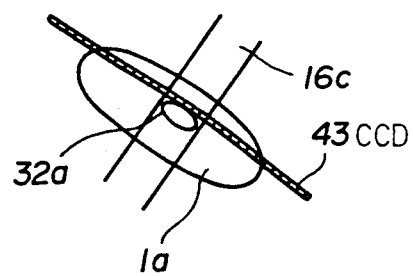

With reference to FIG. 4, the lines of the reticle 36 which intersect at right-angles can be differentiated, and the intersecting portion coincides with the center of an aperture 32a in the ring mirror 32. The reticle 36 can be rotated about the intersecting portion. Rotation of the reticle 36 to align it with a blood vessel 16c, as shown in FIG. 4, produces a synchronous rotation of the cylindrical imaging lenses 42a and 42b and the CCD 43, automatically orienting the CCD 43 perpendicularly to the image of the blood vessel. FIG. 5 illustrates the eye fundus image that will thus be formed on the face of the CCD 43. In the drawing, la denotes the area illuminated by the laser beam.

Because the diameter of speckles, the boiling motion of the speckle pattern and the sensitivity of the CCD 43, the cylindrical imaging lenses 42a and 42b are set so that the image of the eye fundus is formed on the CCD 43 with a lower magnification when it is in a direction parallel to the blood vessel 16c than when it is orthogonal to the blood vessel. As shown in FIG. 5, CCD 43 is provided at a position at which the image of the aperture 32a of the ring mirror 32 does not cross the face of the CCD 43, and the CCD 43 is arranged perpendicularly to the blood vessel 16c of interest.

For photography purposes a swingable mirror 27 is pivoted about a point 27a in the direction indicated by the arrow to raise it to a position 27', whereby the observation and photographic light including speckle light from the eye fundus that is reflected by the swingable mirror 27 and forms an image which is photographed on photographic film 28. Thus, the system can be used for observation and photography of the eye fundus like an ordinary fundus camera. The ability to observe and photograph the eye fundus when it is being illuminated by the laser beam is desirable, as it enables the point of measurement to be directly confirmed and filmed.

In a system for receiving speckle light from the eye fundus and reflected light for observation and photography, light passing through the aperture 32a of the ring mirror 32 forms an image of the eye fundus 16b at a pinhole aperture 38. The light from the pinhole aperture 38 passes through an interference filter 39 and, when measurement is started, is received by a photomultiplier 40 which outputs a speckle signal to an analysis section 41. The interference filter 39 blocks light having a wavelength other than the 632.8 nm red light produced by the He-Ne laser.

The swingable mirror 30 is provided in the system for receiving speckle light from the eye fundus and light for observation and photography for positional correction purposes so that the image of the blood vessel in the eye fundus 16b is formed at the pinhole aperture 38 after passing through the ring mirror 32. Prior to the start of measurement, this adjustment is effected via the output section 46 using a means such as a trackball 17.

As described above, the trackball 17 is also used for operating the swingable mirror 8 prior to the measurement. A switch or other such means may be provided to switch trackball control between the swingable mirror 8 and the swingable mirror 30. The swingable mirror 30 can be controlled by any ordinary means which allows independent control of the angle of mirror deflection in the x and y directions relative to the optical axis. This applies also to the swingable mirror 8.

To minimize the discrepancy that has to be corrected arising from differences in laser beam deflection angles in the x and y directions, the angle at which the laser beam is reflected by the swingable mirror 30 is made as small as space will permit.

By locating the swingable mirror 30 at a position that is substantially a conjugate of the cornea 16a or pupil of the eye, the mirror 30 can be deflected to move the eye fundus 16b image at the pinhole aperture 38 without the beam being blocked by the pupil or other portion of the eye.

In the light receiving system the imaging lens 25 is a wide angle type, wide enough to provide a view which allows all of the image of the eye fundus 16b to be checked. The imaging lens 26 is a narrow angle type with a high magnification factor which provides a magnified image to facilitate alignment of the blood vessel image in the area illuminated by the laser beam with the pinhole aperture 38.

The imaging lenses 25 and 26 are arranged so that they can be switched instantaneously without moving the optical axis. This variable power lens arrangement facilitates accurate beam alignment with the required measurement position.

The diameter of the ring mirror 32 is just large enough to allow the passage of the light beam from the blood vessel 16c of interest, and the ring mirror 32 is located at a position that is substantially a conjugate of the eye fundus 16b. This assures that the examiner can align the system accurately by manipulating the image of the blood vessel of interest so that the image overlays the aperture of the ring mirror 32. FIG. 4 shows the image that this will produce. As the wavelength separation mirror 34 passes a small amount of speckle light, it is possible for the examiner to confirm the position of the illuminated area 1a.

When measurement is started, speckle light is received by the CCD 43 which outputs a signal to a signal processor 44. The signal processor 44 produces a blood vessel discrimination signal which is converted to a digital signal and output. If the blood vessel has moved because of movement of the eyeball, for example, the amount of this movement is detected from the digital blood vessel discrimination signal by an arithmetic unit 45 which computes a correction amount for compensation for the movement of the blood vessel. The computation result is output to the output section 46 which uses feedback correction to control the swingable mirror 30 and swingable mirror 8 so that the image of the eye fundus is constantly maintained at the same position at the pinhole aperture 38 and the laser beam continues to illuminate the same region in the eye fundus 16b.

The arithmetic unit 45 further serves to distinguish the blood vessel parts on the basis of the blood vessel discrimination signal and to calculate the blood vessel diameter. After calculation the results are output to the output section 46, which then displays the blood vessel diameter on a display.

Observation and photography light (other than red component light) together with the small amount of speckle light is transmitted by the wavelength separation mirror 34 and forms an image of the eye fundus at the reticle 36 also during the measurement process, and can therefore be observed by the examiner. The ability to thus observe the eye fundus during blood flow measurement is highly effective for preventing errors, as it enables any deviation from the area of interest to be observed.

Figure 6:
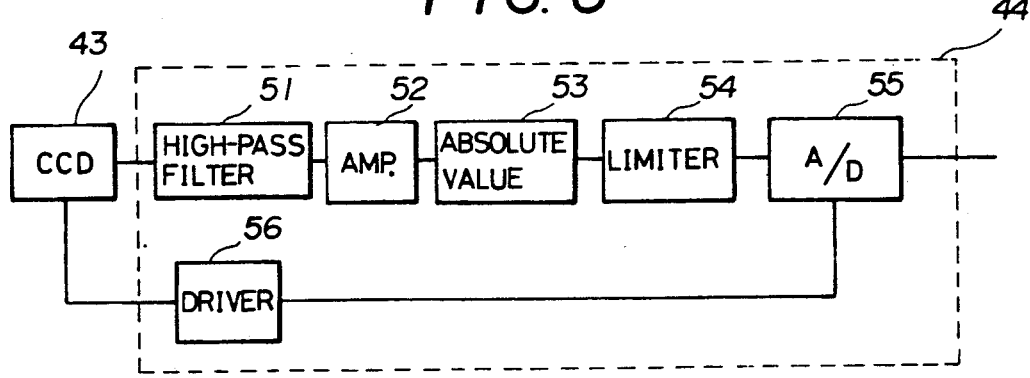
FIG. 6 is a block diagram of a signal processor used in the embodiment.

The electrical system from the signal processor 44 onwards will now be described. FIG. 6 is a schematic diagram of the signal processor. With reference to the drawing, the signal processor 44 is constituted of a drive circuit 56, a high-pass filter 51, an amplifier 52, an absolute value circuit 53, an amplifier with limiter 54 and an A/D converter 55. Drive pulses generated by the drive circuit 56 are input to a 1,024-pixel linear CCD 43. The CCD 43 converts to the speckle light to obtain a speckle signal which is passed through the high-pass filter 51 to extract just the high frequency components. This high frequency component signal is then amplified by the amplifier 52 and passed through the absolute value circuit 53 to obtain an absolute value.

Figure 7:
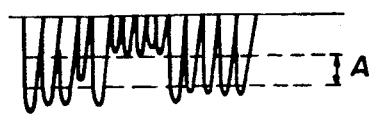
FIG. 7 shows the waveform of the signal output of an absolute value circuit.
Figure 8:
FIG. 8 shows the waveform of the signal output of amplifier with limiter of the embodiment.

The output signal thus obtained from the absolute value circuit 53 is illustrated in FIG. 7. The signal waveform shown is only that obtained from the central area of the CCD, not the whole area of the CCD; this also applies to FIGS. 8, 12 and 13. The signal is then input to the amplifier with limiter 54 to extract a blood vessel discrimination signal by selectively amplifying the required portions such as the portion A shown between the dotted lines in FIG. 7, the other, unnecessary parts being cut off by the limiter. The signal output by the amplifier 54 is illustrated in FIG. 8. The blood vessel discrimination signal thus obtained is converted to digital form by the A/D converter 55 and input to the arithmetic unit 45.

In the arithmetic unit 45 the digital signal data is stored in memory. Assuming that the CCD is composed of n pixels so that n data elements are stored in memory, and an address is assigned to each data element read out of memory, the address of the first data element to be read out would be 0 and that of the nth data element would be n−1. Data from the blood vessel portion will have a high value and data from portions other than the blood vessel will have a low value. To simplify the explanation, data obtained from the blood vessel will be assigned a value of 1 and data obtained from other locations will be assigned a value of 0. While read-out data from the blood vessel will have a value of 1, the effect of the speckles will be that data which is not from the blood vessel will sometimes have a value of 1 and sometimes 0.

Figure 9:
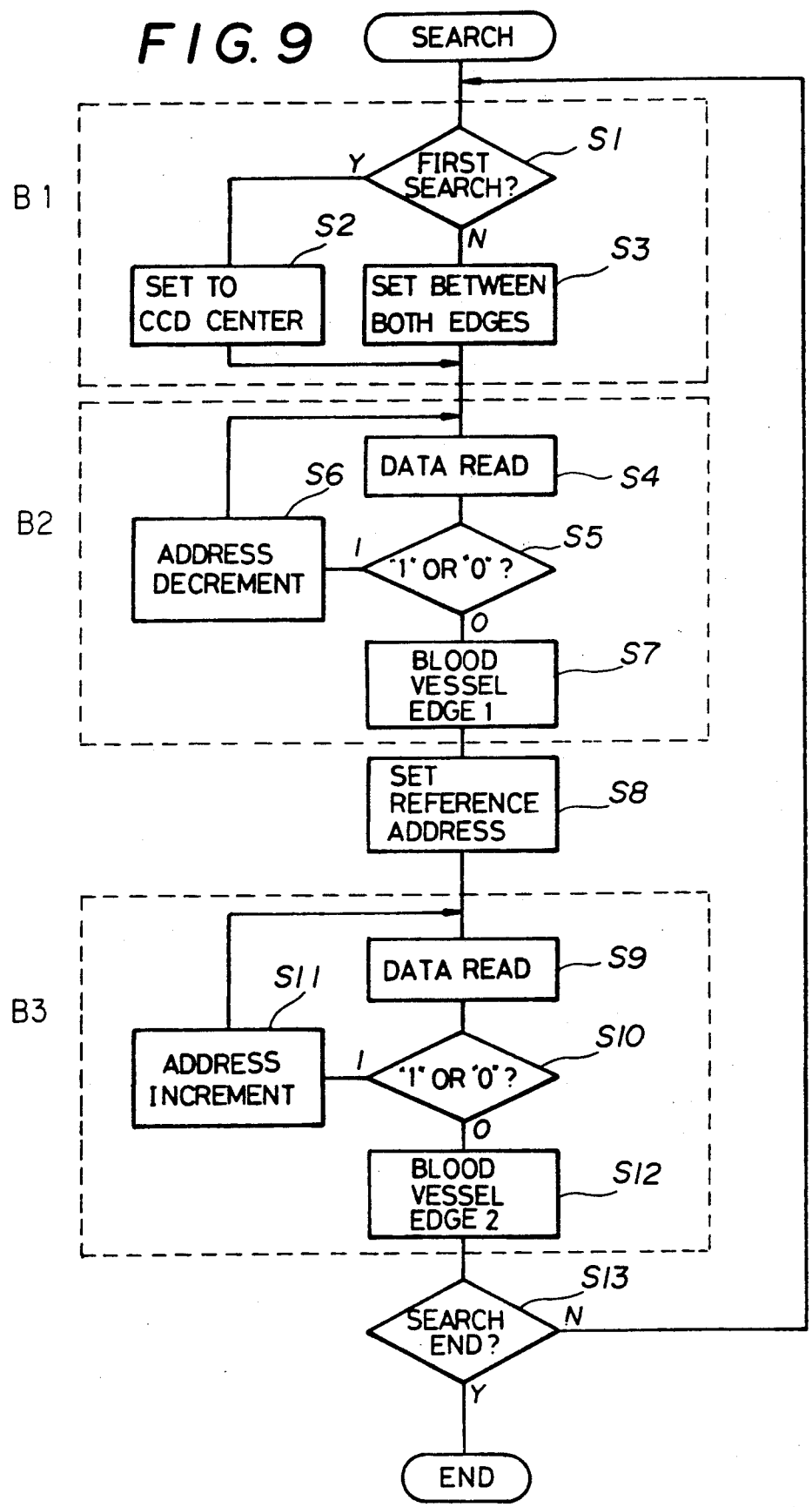
FIG. 9 is a flow chart of the control process for finding a blood vessel.

A method of reducing the effect of speckles will now be described with reference to the blood vessel search procedure illustrated by the flow chart of FIG. 9.

In block B1 the reference position is set for the blood vessel search. During the first search the examiner will have aligned the system beforehand so that the blood vessel crosses the center part of the CCD 43. This means that during the first measurement data from the center of the CCD will have a value of 1, signifying a blood vessel. However, starting with the second search, movement of the blood vessel will gradually shift it from the center of the CCD, making it necessary to move the reference point to the center of the CCD. In block B1 step S1 it is determined whether a search is a first search or a second or subsequent search. If it is determined that it is a first search, in step S2 the reference point is set to the center address of the CCD; if it is a second or subsequent search, in step S3 the reference point is set to a position midway between the edges obtained in the preceding step.

The edges are established by blocks B2 and B3. If the left edge is searched for in block B2, the right edge will be searched for in block B3, and vice-versa. In step S4 the data corresponding to the address is read out, and in step S5 it is determined whether the data has a value of 1 or 0. Since, on the basis of block B1, it can be reliably assumed that the reference address is over the blood vessel, in step S6 the address is decremented and the point at which the data value first changes from 1 to 0 is determined as edge 1 of the blood vessel. In step S7 the position of edge 1 of the blood vessel is detected and stored as blood vessel edge data.

In steps S9 to S12 the same process is used to detect the position of edge 2 and stored the information as blood vessel edge data. In the present method, the edges of the blood vessel are searched for starting from the center of the blood vessel, so that the number of data elements that need to be read out is greatly reduced together with the effect of speckles, since it is only necessary to read out data corresponding to the portion of the diameter of the blood vessel concerned. This enables the determination process to be carried out quickly and reliably, as compared with the method in which searches proceed sequentially from address 0 to $n-1$ and the data has to be examined each time to ascertain whether it represents speckles or the presence of a blood vessel.

The diameter of the thus identified blood vessel can be determined by multiplying the width between both edges of the blood vessel with a coefficient determined by the magnification of the light receiving system. It is preferable to obtain the width of the identified blood vessel several times and to derive therefrom an average value or the smallest of the measured widths of the blood vessel for improvement in determining the blood vessel diameter.

A plurality of positional information is required if the amount by which the blood vessel has shifted is to be obtained just on the basis of blood vessel edge information. Also, this information will be affected to some extent by speckles It is therefore necessary to obtain information from at least three edge searches in order to determine the movement of the blood vessel. By comparing the difference between the (m)th and (m+1)th data with the difference between the (m+1)th and (m+2)th data, it becomes possible to check whether or not there has been movement of the blood vessel in the period from the acquisition of the (m)th data to the (m+2)th data. If it is determined that there has been movement, it is possible to determine the amount of movement by, for example, obtaining the weighted averages of the differences. Correction is not required if there has been no movement, therefore, a method shall now be explained which consists of taking the smallest of the differences as the amount of movement.

Figure 10:
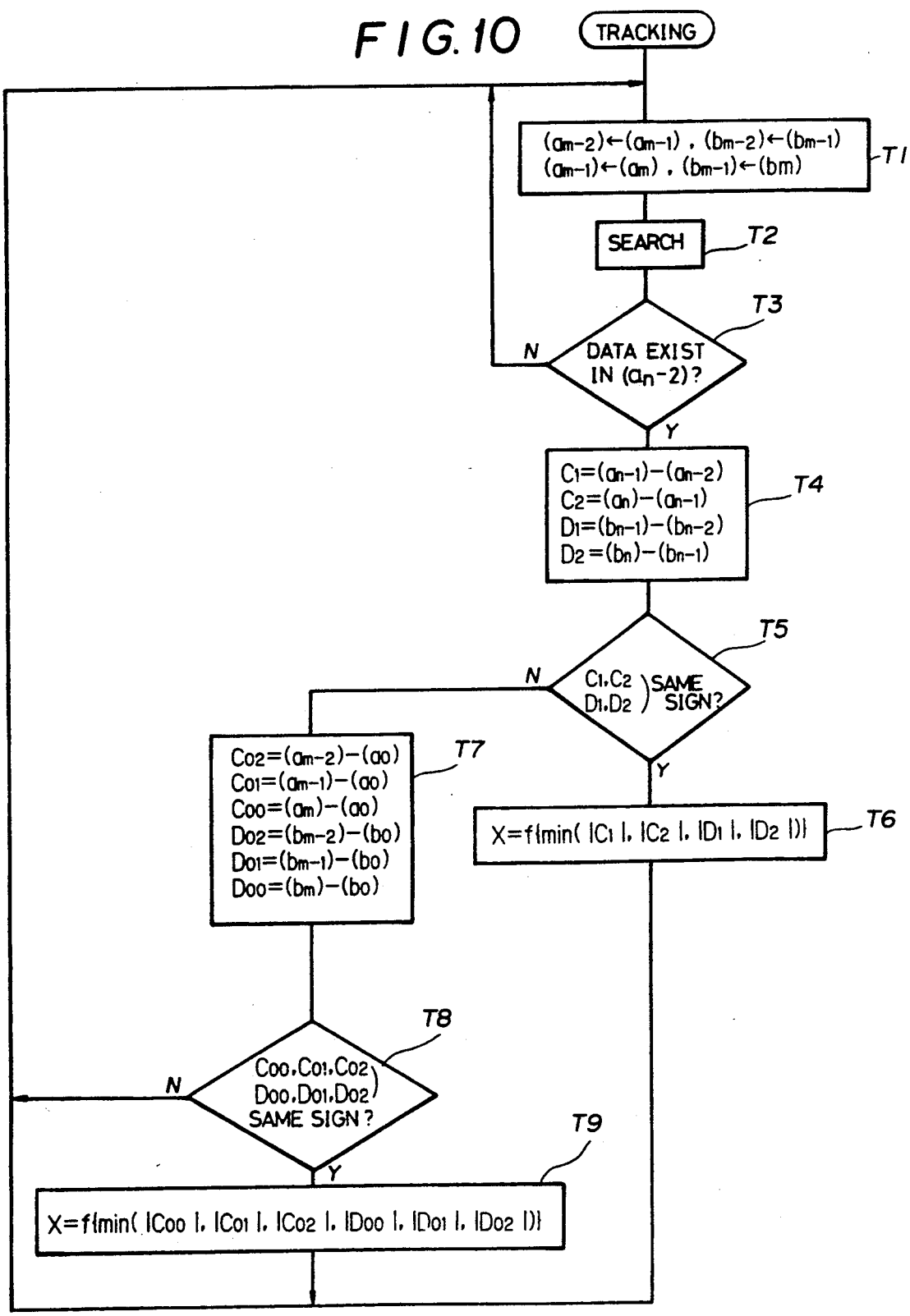
FIG. 10 is a flow chart of the control process for tracking a blood vessel.

FIG. 10 is a flow chart of a process for determining the amount of blood vessel movement in accordance with this method. In step T1 the data up to the preceding two searches is stored prior to the data being updated. Step T2 is a blood vessel search, the details of which are as described with reference to the flow chart of FIG. 9. In this step, fresh blood vessel edge data is incorporated. In step T3 it is determined whether or not sufficient data has been prepared to enable the amount of movement to be obtained. If there is not enough data the process returns to step T1; if the data is sufficient the process advances to step T4. In step T4 differences C1, C2, D1, D2 between consecutive data sets are obtained for both edges, and in step T5 the presence or absence of movement is determined by determining whether or not the differences C1, C2, D1, D2 have the same sign, which is to say, whether or not the movement has been in the same direction in each case.

If the signs are the same and it is determined that movement has taken place in the same direction in each case, the process advances to step T6. If the signs are different and it is therefore determined that movement has not taken place in the same direction, the process moves to step T7. In step T6 the minimum value among C1, C2, D1, D2 is taken as the amount of movement, and after computing the amount of correction, taking into consideration the magnification and other such optical system factors, the necessary correction amount for returning the blood vessel to the initial position is obtained and output.

Step T7 is for when the movement of the blood vessel is so small that it is not detected from just one or two searches. In such a case, in step T7 the discrepancies C02, C01, C00, D02, D01, D00 between the initial positions (a0, b0) and each edge $(a_m, b_m)$, $(a_{m-1}, b_{m-1})$, $(a_{m-2}, b_{m-2})$ are obtained. The signs of C02, C01, C00, D02, D01, D00 are determined in step T8. The signs all being the same will signify that there has already been a shift to one side from the initial position, and the process advances to step T9, while if there are differences among the signs it will be unclear whether or not movement has taken place to one side from the initial position, so the process will return to step T1. In step T9 the minimum of the discrepancy values C02, C01, C00, D02, D01, D00 is taken as the amount of deviation and a correction amount is obtained and output.

In the output section 46 a pulse motor is driven by an amount that is in accordance with the correction amount output by the arithmetic unit 45, controlling the swingable mirrors 8 and 30 linked to the pulse motor. For automatic tracking, the swingable mirror 8 is driven to move the laser beam to the center of the blood vessel concerned. Likewise, the swingable mirror 30 is drive to implement automatic tracking by moving the speckle pattern observation point to the center of the blood vessel concerned.

When information is being obtained from a blood vessel in the eye fundus, in some cases there will be differences between measured values obtained from the center and the edges of a blood vessel. Central position correction is used to eliminate variance caused by such a difference.

FIG. 11 is a flow chart illustrating the central position correction procedure. In step R1 the position of the blood vessel is detected, and in step R2 the position of the blood vessel is detected continuously until the examination is started. In step R3 the central position of the blood vessel is obtained from the most recent blood vessel position information immediately following the start of examination, the degree of discrepancy between this position and the central position of the CCD 43 is obtained and a correction is applied to eliminate any positional discrepancy between the blood vessel center and the CCD center. In step R4 the initial position of the blood vessel is set so that the blood vessel center coincides with the CCD center. In accordance with the initial position set in step R4, in step R5 positional correction is applied constantly to ensure that the center of the blood vessel coincides with the central position of the CCD 43, and this continues until examination is terminated in step R6. With this method, even if the system alignment by the examiner is off-center of the blood vessel, it will still be possible to examine the blood vessel center immediately following the start of the examination.

As described above, as the system is arranged so that when the reticle 36 is rotated relative to the optical axis the CCD 43 also rotates relative to the optical axis, the CCD can be set perpendicularly to the blood vessel. A potentiometer 47 is provided for detecting the angle of rotation of the CCD. An angle detection section 48 applies 8-bit A/D conversion to the output of the potentiometer 47 to obtain angle data, which is input to the arithmetic unit 45 to determine the rotation angle of the CCD. The arithmetic unit 45 calculates and outputs correction amounts to be applied in the x and y directions to correct for movement of the blood vessel.

It will not be possible to obtain a good speckle signal if there is a large discrepancy between the size of speckle images on the CCD 43 and the size of the CCD's pixels. As shown in FIG. 12a, speckles 93' which are larger than one of the pixels G of the CCD 43 will reduce the amount of incident light on the pixels, making it impossible to obtain a sufficiently strong speckle signal. FIG. 12b shows the type of speckle signal 93a that will result in such a case. On the other hand, speckles 93' which are small compared to the pixels G of the CCD 43, as shown in FIG. 12e, the amount of incident light on the pixels will be averaged out, producing the kind of speckle signal 93a shown in FIG. 12f which lacks contrast. Speckles which are more or less the same size as the pixels as shown in FIG. 12c will produce a good speckle signal such as the signal 93a shown in FIG. 12d.

A method of using speckle signals as a basis for discriminating objects traveling at different speeds will now be described. Speckles which have a boiling motion require a complex explanation, so for the sake of simplicity the method will be explained in terms of translational motion. The left half of FIG. 13a depicts blood cells in tissues in the vicinity of the blood vessel which have a low travel speed, so the speckles 93' also show a low travel speed. The right half of the drawing depicts blood cells with a high travel speed such as the blood cells in a blood vessel, and which therefore give rise to speckles with a high travel speed. FIG. 13b shows the waveform of the corresponding signals output by a photosensor (i.e. a CCD). If the speed of the speckle pattern is higher than the scanning speed of a scanning sensor, large numbers of dark and light parts of speckles 93' will pass through the light receiving part of the CCD 43, giving rise to an output in which the light and dark portions are averaged and there is little difference between signals generated at different light receiving points.

On the other hand, if the speed of the speckle pattern is lower than the scanning speed of the scanning sensor, the number of dark and light parts of the speckles 93' passing through the light receiving part of the CCD 43 will decrease, so a strong signal will be output from a point on the light receiving part of the CCD 43 through which more light speckle portions pass, and a weak signal will be output from a point through which more dark speckle portions pass. Therefore, by optimizing the scanning speed of the scanning sensor with respect to speckle patterns arising from objects moving at different speeds and obtaining the intensity ratio of signals output by the scanning sensor, it becomes possible to discriminate between objects traveling at different speeds.

If, as shown in FIG. 5, with respect to the blood vessel image formed on the CCD 43, the ratio between the image in a direction parallel to the blood vessel 16c and the image in a direction perpendicular to the blood vessel is altered to compress it in the direction parallel to the blood vessel, the amount of incident light on the CCD 43 is increased without degradation of resolution in the direction perpendicular to the blood vessel. There will be a slight degradation in the signal intensity ratio of the light and dark speckle portions, but as there will be a considerable decrease in the dark portions, there will be few discrimination errors.

FIGS. 14 to 21 relate to other embodiments which have the same object as the embodiment described above but are not based on the optical system of a fundus camera. In the descriptions, parts that are the same as parts in the above embodiment have been given the same reference numerals, and a detailed description of such parts is omitted.

Figure 15:
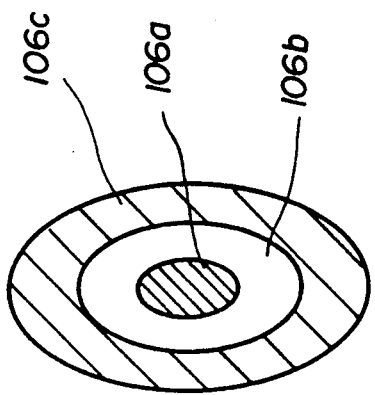
FIG. 15 shows details of a movable mirror.
Figure 14:
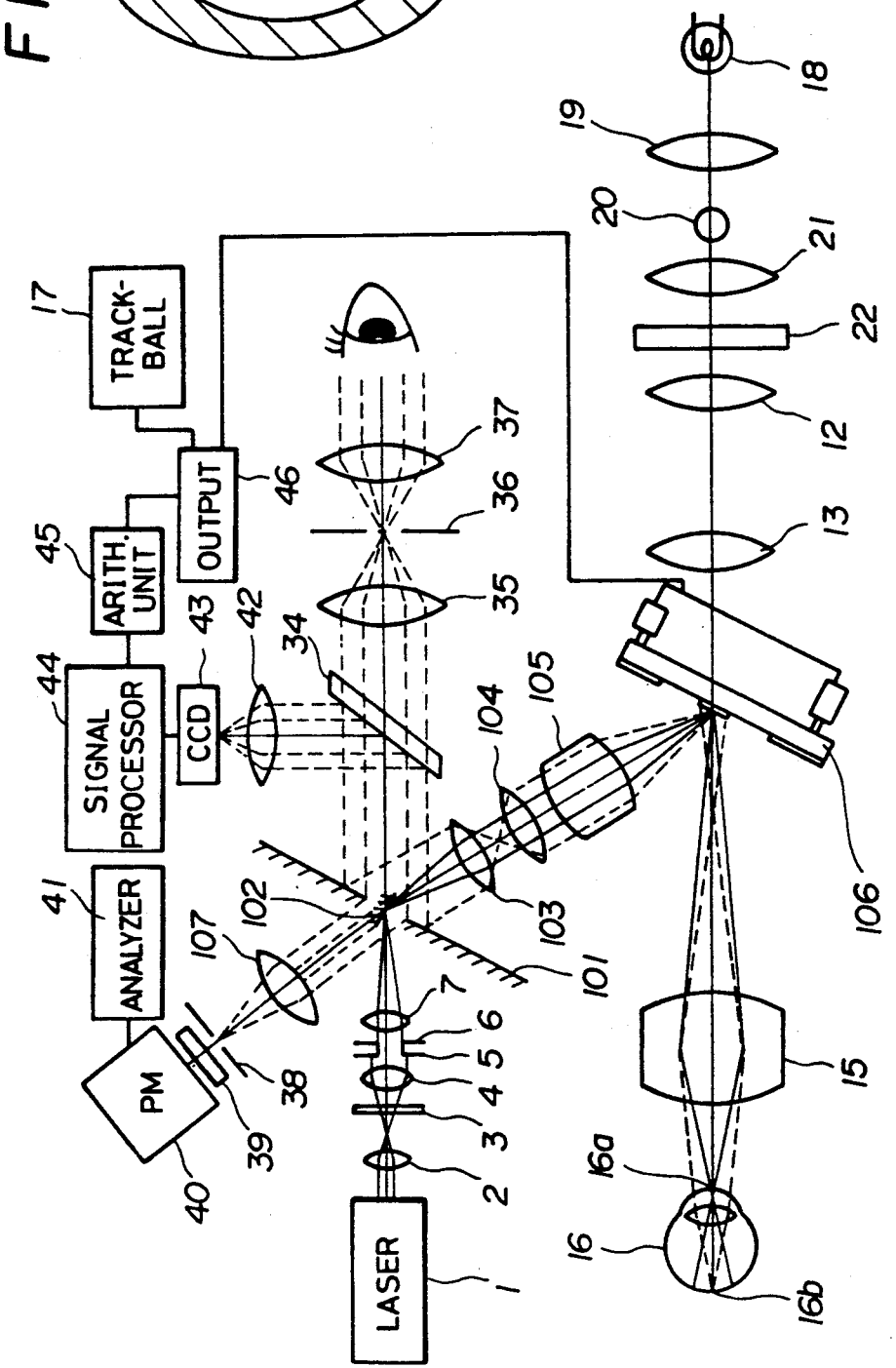
FIG. 14 is a schematic view of another embodiment of the apparatus of the invention.
Figure 18A:
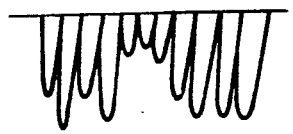
FIGS. 18a to 18d show waveforms of CCD output signals.
Figure 18B:
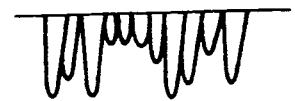

With reference to FIG. 14, a laser beam is converged on a small mirror 102 located at a position that is a conjugate of the cornea 16a. The light passes through relay lenses 103 and 104 and a focusing lens 105, is reflected by a swingable mirror 106 located at a position that is a conjugate of the cornea 16a and is projected into the eye fundus 16b via the objective lens 15. As shown in FIG. 15, the swingable mirror 106 is constituted of a total reflection mirror 106a, a transparent section 106b and a portion 106c with a low reflectance that does not transmit light.

Part of the light which is scattered and reflected by the eye fundus 16b passes back along the same light path, is reflected by a ring mirror 101 and forms an image on the CCD 43. Light that is passed by the ring mirror 101 and the small mirror 102 is formed into an image at the pinhole aperture 38 by an imaging lens 107.

In the first embodiment the mirror used for beam alignment and tracking and the mirror used for observation-point alignment and tracking move independently, a drawback of which is that it complicates the alignment operation. In addition, during tracking the mirrors would sometimes move out of mutual alignment. To solve such problems, in this embodiment the function of the two mirrors have been integrated into a single mirror.

FIG. 16 is a schematic diagram of a signal processor comprised of a selector 57, memory 58, data latch 59, size comparator 60 and controller 61. The controller 61 controls the timing at which memory 58 reads and writes. The preceding read from the memory 58 is latched by the data latch 59. A size comparison is made between the value of this data and the value of the preceding data converted to 8-bit digital form by the A/D converter 55. Data which in accordance with the decision of the size comparator 60 has a large value is selected by the selector 57 and written into the memory 58, the preceding data being erased in the process. This is carried out with respect to the values of all the signals output by the CCD 43. This is done a plurality of times and the 8-bit digital blood vessel discrimination signal is output to the arithmetic unit. This processing compensates for the dark parts of the speckle signals to provide a more faithful blood vessel discrimination signal.

Figure 18C:

The same effect can be obtained with the signal processor arrangement shown in FIG. 17. In this arrangement two CCDs 43 and 43' are provided to receive eye fundus images. The outputs from the CCDs 43 and 43' are passed through corresponding high-pass filters 51, 51' and amplifiers 52, 52', resulting in the type of output signals shown in FIGS. 18a and 18b. The outputs of respective absolute value circuits are input to a size comparator 62, which selects and outputs the strongest of these input signals. FIG. 18c shows an output waveform of the size comparator 62.

Figure 18D:

Output signals from the size comparator 62 are input to the amplifier with limiter 54 where the required parts of the signals are amplified and the unnecessary parts suppressed by the limiter, thereby producing the signal waveforms shown in FIG. 18d and extracting blood vessel discrimination signals. This embodiment has been described with reference to the use of two CCDs, but the invention is not limited to two; the same effect can be obtained with a larger number. For the CCD 43 shown in FIG. 16, an area sensor may be used instead of a linear sensor and the same effect obtained by the addition of a linear sensor's multiple lines.

Figure 19:
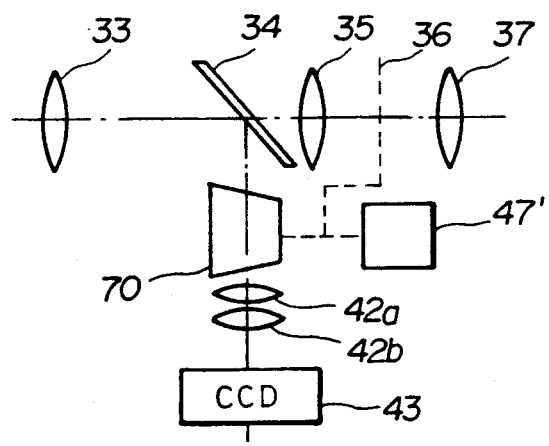
FIG. 19 shows the arrangement of an image rotator.

An image rotator 70 may be used to arrange the blood vessel image in perpendicularly relative to the CCD 43. With reference to FIG. 19, the blood vessel image formed on the face of the CCD 43 may be rotated instead. The image rotator is linked to the reticle 36 so that both rotate together For angular data, a potentiometer 47' is provided for detecting the angle of rotation of the image rotator.

Figure 20:
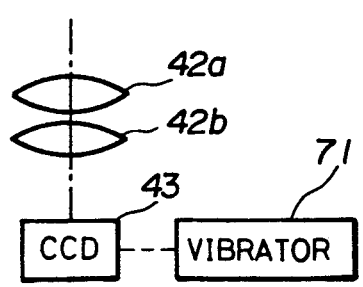
FIGS. 20 and 21 show an arrangement for oscillating an image on the CCD.
Figure 21:
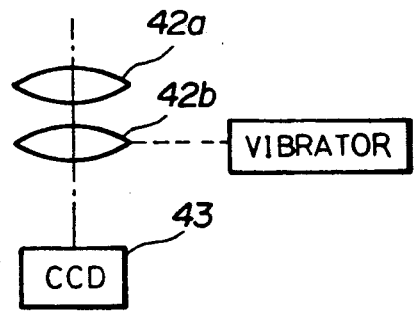

With reference to FIG. 20, the CCD 43 may be oscillated by a vibrator 71 at a low frequency and amplitude compared to the movement of speckles in the direction of the blood vessel the image of which is formed on the CCD. Alternatively, the vibrator 71 may be arranged so that it oscillates the lens 42b disposed in front of the CCD. Even with the use of oscillations having a low frequency and amplitude compared to the movement of speckles, the effect obtained will be the same as when the image is compressed in a direction parallel to the blood vessel.

When the CCD 43 is a linear sensor, no resolution is required in a direction parallel to the long axis of the blood vessel the image of which is produced by the laser speckle light. Therefore, the compression along the long axis of the blood vessel can be effected at the Fourier plane, but it must be effected at the image plane in the direction perpendicular to the blood vessel because it needs resolution.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmological measurement method, comprising the steps of: projecting a laser beam having a predetermined diameter to an eye fundus; detecting motion of a laser speckle patter formed by laser light scattered and reflected from the eye fundus at an observation point as fluctuations in the speckle light intensity; producing a speckle signal from the fluctuations in the speckle light intensity; evaluating the speckle signal to discriminate differences in travel velocities of blood cells in the eye fundus to identify a blood vessel part of the eye fundus; determining any movement of the identified blood vessel part of the eye fundus by finding both edges of the identified blood vessel and determining a difference between positions of the edges over time to determine the amount of movement of the identified blood vessel part; and adjusting the position of the region illuminated by the laser beam and the position of the observation point by an amount corresponding to the amount of blood vessel movement to automatically track the blood vessel part.

2. An ophthalmological measurement method according to claim 1 wherein the step of detecting motion includes receiving the laser speckle pattern at a magnification, and further comprising the step of determining a diameter of the blood vessel by multiplying a distance between both the edges of the blood vessel with a coefficient dependent on the magnification at which the laser speckle pattern is received.

3. An ophthalmological measurement method according to claim 1, wherein the edges of the blood vessel part are found by searching outward from the center of the observation point.

4. An ophthalmological measurement method according to claim 1, wherein the automatic tracking is implemented by moving the blood vessel image to be tracked to the speckle pattern observation point.

5. An ophthalmological measurement method according to claim 1, wherein the position of the region illuminated by the laser beam automatically tracks the center of the blood vessel to be tracked.

6. An apparatus for automatically tracking a blood vessel in an eye fundus; comprising:
projecting means for projecting a light beam at an observation point of an eye fundus to generate a speckle pattern;
evaluating means for evaluating the speckle pattern to discriminate differences in travel velocities of blood cells in the eye fundus to identify edges of the blood vessel and including means for determining differences between positions of the edges over time to determine an amount of movement of the blood vessel; and
positioning means responsive to an output from the evaluating means for continuously positioning the projecting means to project the light beam at the blood vessel, whereby the movement of the blood vessel is automatically tracked.

7. An apparatus for automatically tracking a blood vessel according to claim 6; wherein the means for determining differences determines differences at least between a first edge position and a second edge position to generate a first difference signal and between the second edge position and a third edge position to generate a second difference signal; and the evaluating means comprises means for comparing the first difference signal with the second difference signal to determine the amount of movement of the blood vessel.

8. An apparatus for automatically tracking a blood vessel according to claim 6; wherein the evaluating means further includes light receiving means for receiving the speckle pattern; and the positioning means includes means for automatically positioning the light receiving means to automatically track the movement of the blood vessel.

9. An apparatus for automatically tracking a blood vessel according to claim 6; wherein the evaluating means includes light receiving means for receiving the speckle pattern at a magnification, and means for determining a diameter of the blood vessel by multiplying a distance between the edges of the blood vessel with a coefficient dependent on the magnification of the light receiving means.

10. An apparatus for automatically tracking a blood vessel according to claim 6; wherein the evaluating means includes means for identifying the edges of the blood vessel by searching outward from the center of the observation point to locate the edges of the blood vessel.

11. An ophthalmological measurement apparatus in which an eye fundus is illuminated by a laser beam having a predetermined diameter and in which motion of a laser speckle pattern formed by laser light scattered and reflected from the eye fundus is detected at an observation point as fluctuations in the speckle light intensity to produce a speckle signal which is evaluated for ophthalmological measurement, comprising:

an optical system for projecting a laser beam to a region of the eye fundus including a blood vessel;

means for detecting movement of a laser speckle pattern formed by light scattered by the eye fundus as fluctuations in the light intensity of the speckles at an observation point;

means for identifying blood vessel parts in the eye fundus and for identifying edges of the blood vessel parts by discriminating differences in the travel velocities of blood cells in the eye fundus from speckle signals obtained from the detecting means;

means for determining the amount of any movement the blood vessel part makes by determining a difference between positions of the edges over time; and means for automatically tracking the blood vessel part depending on the determined amount of blood vessel movement by adjusting the position of the region illuminated by the laser beam and adjusting the position of the observation point.

12. An ophthalmological measurement apparatus according to claim 11, further comprising a mechanism for deflecting the laser beam into alignment with the blood vessel to be tracked.

13. An ophthalmological measurement apparatus according to claim 12, wherein the mechanism includes a mirror for deflecting the laser beam.

14. An ophthalmological measurement apparatus according to claim 11, wherein a scanning sensor is provided at the observation point for detecting fluctuations in speckle light intensity.

15. An ophthalmological measurement apparatus according to claim 14, further comprising a plurality of scanning sensors and circuitry for selecting the output with the maximum value among the outputs of the sensors.

16. An ophthalmological measurement apparatus according to claim 11, wherein the means for automatically tracking includes a first mirror for deflecting the laser beam into the blood vessel for adjusting the region illuminated by the laser beam and a second mirror for deflecting a blood vessel image for adjusting the position of the observation point.

17. An ophthalmological measurement apparatus according to claim 11, wherein the means for automatically tracking includes a single mirror for deflecting the laser beam into the blood vessel for adjusting the region illuminated by the laser beam and for deflecting a blood vessel image for adjusting the position of the observation point.

* * * * *